(12) United States Patent
Lu et al.

(10) Patent No.: US 8,673,641 B2
(45) Date of Patent: Mar. 18, 2014

(54) ON-LINE DETECTION METHOD OF CHROMIUM-FREE COATING FILM THICKNESS ON SURFACE OF STRIP STEEL

(75) Inventors: Yongqiang Lu, Shanghai (CN); Chunguo Lv, Shanghai (CN); Zhicheng Wang, Shanghai (CN)

(73) Assignee: Baoshan Iron & Steel Co., Ltd., Shanghai (CN)

( * ) Notice: Subject to any disclaimer, the term of this patent is extended or adjusted under 35 U.S.C. 154(b) by 0 days.

(21) Appl. No.: 13/529,863

(22) Filed: Jun. 21, 2012

(65) Prior Publication Data

US 2012/0324992 A1    Dec. 27, 2012

Related U.S. Application Data

(63) Continuation of application No. PCT/CN2011/073425, filed on Apr. 28, 2011.

(30) Foreign Application Priority Data

Nov. 26, 2010    (CN) .......................... 2010 1 0561145

(51) Int. Cl.
    *G01B 21/08*    (2006.01)
(52) U.S. Cl.
    USPC ................................ 436/2; 73/61.62; 702/97
(58) Field of Classification Search
    USPC .................................. 436/2; 73/61.62; 702/97
    See application file for complete search history.

(56) References Cited

U.S. PATENT DOCUMENTS

2009/0306923 A1* 12/2009 Keller et al. .................... 702/97

FOREIGN PATENT DOCUMENTS

| CN | 1407335 A | 4/2003 |
| CN | 101135049 A | 3/2008 |
| JP | 2004-285290 A | 10/2004 |

OTHER PUBLICATIONS

International Search Report Dated Sep. 8, 2011, issued in related International Patent Application No. PCT/CN2011/073425.

* cited by examiner

*Primary Examiner* — Monique Cole
(74) *Attorney, Agent, or Firm* — Kilpatrick Townsend & Stockton LLP

(57) ABSTRACT

A measuring method of chromium-free coating film thickness on surface of strip steel comprising selecting two water-soluble chemical substances containing elements P, Ca, Ti, Ba or Sr and not reacting with a chromium-free coating liquid; adding the chemical substances into the chromium-free coating liquid and agitating them to be homogeneous, thereafter, fabricating a reference sample of coating film; using a ray emitted by an off-line film thickness instrument to excite the two water-soluble chemical substances so as to obtain characteristic spectrums to obtain a correction function expression between the measured film thickness and the thickness correction value by fitting; adding the water-soluble chemical substance which has a weak characteristic spectrum into a chromium-free coating liquid, and using the expression to obtain the actual coating film thickness. The method is capable to monitor film thickness with no adverse effect on adhesiveness and corrosion-proof of the coating film.

3 Claims, 1 Drawing Sheet

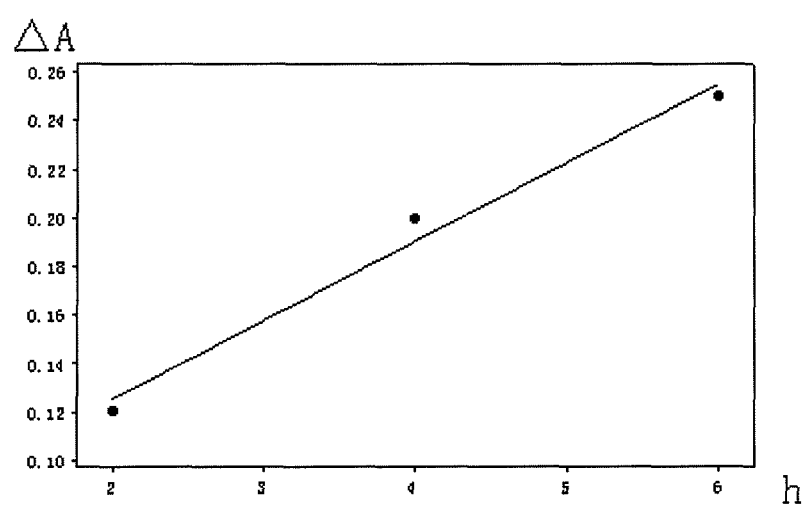

ON-LINE DETECTION METHOD OF CHROMIUM-FREE COATING FILM THICKNESS ON SURFACE OF STRIP STEEL

FIELD OF THE INVENTION

This invention relates generally to measurement of coating film thickness on surface of strip steel, and particularly, to a measuring method of chromium-free coating film thickness on surface of strip steel.

BACKGROUND OF THE INVENTION

In the situation that environment protection is increasingly concerned, and the voice for the chromium-free green product is stronger and stronger. The major steelworks in the world are all active to develop chromium-free coatings to substitute chromate coatings for the film of their products.

To apply chromium-free coating film onto the surface of strip steel is rather difficult because there are not good methods and standards for both preparation of chromium-free coating liquid and detection of chromium-free coating film thickness. Especially for large-sized electric machines, after a number of laminates of strip steel sheet is stacked together, uneven thickness of coating film of a laminate or laminates will result in an uneven thickness of the whole stack of laminates. Therefore, how to accurately detect coating film thickness and how to optimize application process of coating film are both stiff challenges in production of strip steels with chromium-free coating film.

In the case of on-line detection of coating film thickness, the prior arts often use ray inspection methods which inspect characteristic elements. Or the prior arts use X ray fluorescence remitter to perform the on-line or off-line detection. In these detection methods, however, it is necessary for a coating liquid to contain some characteristic element, such as chromium, which is easy to emit X-ray fluorescence when it is excited, and the content of the element must be changeless. Therefore, there are only very few coating films whose thickness can be detected by use of these methods, and each set of detection instrument can detect only one characteristic element and so the thickness of only one type of coating film. For producing various types of different-type coating films, it is necessary to equip with multiple sets of thickness detection instrument, which is inconvenient to use in mass production. Even if a type of coating film is kept unchanged, the relative difference of compositions of different batches of coating films still has a non-negligible effect on detection result. Chromium-free coating film does not contain characteristic element Cr, so those methods are helpless for on-line detecting.

Nowadays, thickness of chromium-free coating film is often detected by means of off-line film thickness detection instruments. The detection instruments largely apply the eddy current principle to carry on detection. It takes specimens from the head end and the tail end of a steel strip and measures thickness at multiple points on the work side, middle side, and the driven side, and then takes an average of all the measurements as the thickness of the whole coating film on the steel strip. The advantages of those methods lie in that it is convenient to carry out measuring at many points; however, in those methods, it is necessary to have a typical sample. In addition, because the off-line detection systems themselves and the film thickness reference card both have rather big errors and it is impossible to implement on-line monitor, those methods are unsuitable to manufacture steel strips through a continuous annealing furnace and are prone to bring about an uneven film.

SUMMARY OF THE INVENTION

The objective of the invention is to provide an on-line detection method of chromium-free coating film thickness on surface of strip steel. The method is to add weak characteristic element into chromium-free coating liquid to obtain a correction function and further to obtain the thickness of the coating film, which does not has a correct measured result, but only has no effect on adhesiveness, corrosion-proof and environmental performance of the coating film.

The objective is achieved by a on-line detection method of chromium-free coating film thickness on surface of strip steel comprises the follows:

Step 1, Selecting two water-soluble chemical substances which contain elements P, Ca, Ti, Ba or Sr and will not react with chromium-free coating liquid;

Step 2, Adding the two water-soluble chemical substances selected in Step 1 into the chromium-free coating liquid and agitating them to be homogeneous, thereafter, fabricating a reference sample of the coating film;

Step 3, Using a ray emitted by an off-line film thickness detection instrument to respectively excite the two water-soluble chemical substances so as to obtain characteristic spectrums and to have the thickness of the reference film sample; the coating film thickness determined by means of the water-soluble chemical substance which has an intensive characteristic spectrum is taken as actual film thickness, whereas the coating film thickness determined by means of the water-soluble chemical substance which has a weak characteristic spectrum is taken as measured film thickness, the difference between the actual film thickness and the measured film thickness is taken as a thickness correction value; via many times of such operation, it is to obtain many thickness correction values corresponding to the many measured film thickness, and a correction function expression between the measured film thickness and the thickness correction value can be obtained by fitting those discrete data;

Step 4, Adding the water-soluble chemical substance which has a weak characteristic spectrum into the chromium-free coating liquid, and using a ray emitted by an on-line coating film thickness detection instrument to excite the water-soluble chemical substance and so to obtain the measured film thickness, and then using the correction function expression to obtain a thickness correction value, finally, actual coating film thickness can be obtained from the measured film thickness and thickness correction value.

The water-soluble chemical substances which will not react with the chromium-free coating liquid are β-sodium glycerol-phosphate, calcium acetate, titaniumocene complexes, barium chloride or strontium acetate;

The ray is $\chi$ ray or $\gamma$ ray. The on-line detection method of chromium-free coating film thickness on surface of strip steel, by means of adding weak characteristic element into chromium-free coating liquid to obtain a correction function is capable to detect thickness of the coating film in time, and to by means of on-line detection, is capable to monitor film thickness effectively and optimize the coating process continuously; and in the meantime, the method is applicable to different-type chromium-free coating liquids with high precision, and has no adverse effect on adhesiveness, corrosion-proof and environmental performance of the coating film

BRIEF DESCRIPTION OF DRAWINGS

FIG. 1 is a curve graph of a function of the measured thickness and the correcting thickness in embodiment 1 of the detection method of chromium-free coating film thickness on surface of strip steel of the invention.

DETAILED DESCRIPTION OF THE INVENTION

The invention is now described in detail with a specific embodiment. It is understood that the embodiment is used only for explaining the invention but not for limiting the scope of the invention. It is also understood that person skilled in the art can make various changes or modifications without departing from the spirit and scope of the invention after having read the description herein, therefore any versions identical or equivalent to the solution herein all fall in the scope defined in the claims of the invention.

Embodiment 1 a detection method of chromium-free coating film thickness on surface of strip steel comprises the following steps:

Step 1: selecting two water-soluble chemical substances which contain elements P, Ca, Ti, Ba or Sr and will not react with a chromium-free coating liquid, in this embodiment, the water-soluble chemical substances are β-sodium glycerol-phosphate, calcium acetate, titaniumocene complexes, barium chloride or strontium acetate.

Step 2: adding the two chemical substances selected in step 1 into the chromium-free coating liquid and agitating them to be homogeneous, thereafter, fabricating a reference sample of the coating film;

Step 3: using $\chi$ ray or $\gamma$ ray emitted by an off-line film thickness instrument to excite the two chemical substance so as to obtain characteristic spectrums, thereby to have the coating film thickness of the reference film sample; the coating film thickness determined by means of the additive which has an intensive characteristic spectrum can be taken as actual film thickness H, whereas the coating film thickness determined by means of the additive which has a weak characteristic spectrum is taken as measured film thickness h, the difference between the actual film thickness H and the measured film thickness h is taken as a thickness correction value $\Delta A$; through many times of such operation, it is possible to obtain many thickness correction values corresponding to the many measured film thickness; a correction function expression between the measured film thickness h and the thickness correction value $\Delta A$ can be obtained by fitting those discrete data.

Step 4: adding the additive which has a weak characteristic spectrum into the chromium-free coating liquid, and using a ray emitted by an on-line coating film thickness instrument to excite the additive and to obtain film thickness, and then using the film correction function expression to obtain a thickness correction value, finally, actual coating film thickness can be obtained from the measured film thickness and thickness correction value.

In the embodiment, for fabricating the reference film sample, the chemical substances, i.e. calcium acetate ((CH3COO)2Ca.H2O) and β-sodium glycerol-phosphate (C3H7Na2O6P.5H2O), which contain Ca, P element, are added by 0.1~1%, by weight percent, into the chromium-free coating liquid; the characteristic spectrums of the two elements are detected by use of a off-line film thickness instrument, thereby the measured film thickness and thickness correction value are obtained which are shown in Table 1.

TABLE 1

| actual thickness obtained by exciting element Ca H (g/m²) | measured thickness obtained by exciting element P h (g/m²) | thickness correction value $\Delta A$ (g/m²) |
|---|---|---|
| 2.01 | 1.89 | 0.12 |
| 4.04 | 3.84 | 0.2 |
| 6.05 | 5.8 | 0.25 |

The curve shown in FIG. 1 is plotted based on the data in Table 1, thereafter, a function expression is obtained by fitting the curve: thickness correction value $$\Delta A = 0.0600 + 0.0325h \tag{1}$$

In mass production of the chromium-free coating film, coating film thickness is detected by using a ray emitted by a on-line film thickness instrument to excite element P, wherein the measured film thickness on the upper surface is 3.16 g/m², and the measured film thickness on lower surface is 3.1 g/m².

Substituting h in expression (1) with the measured film thickness on the upper surface and the lower surface, respectively, the actual film thickness on the upper surface and the lower surface is obtained respectively: 3.32 g/m² and 3.26 g/m².

By comparing between the properties of the coating films of the steel sheets with and not with β-sodium glycerol-phosphate (C3H7Na2O6P.5H2O), it is concluded that to add β-sodium glycerol-phosphate (C3H7Na2O6P.5H2O) has not adverse effect on film properties such as adhesiveness, corrosion resistivity, and so on, as shown in Table 2.

TABLE 2

| film's place | film of comparative object (not added) adhesiveness | film of the invention's embodiment (added with) adhesiveness | film of comparative object (not added) corrosion resistivity | film of the invention's embodiment (added with) corrosion resistivity |
|---|---|---|---|---|
| on upper surface of steel strip | grade 1 | grade 1 | 5% | 5% |
| on lower surface of steel strip | grade 1 | grade 1 | 5% | 5% |

The invention claimed is:

1. An on-line detection method to determine chromium-free coating film thickness on the surface of strip steel, the method comprising:
   (a) selecting a first and a second water-soluble chemical substance which contain elements P, Ca, Ti, Ba or Sr and do not react with a chromium-free coating liquid;
   (b) adding the two water-soluble chemical substances selected from step (a) into the chromium-free coating liquid and agitating them to be homogeneous,
   (c) fabricating a reference sample of the coating film on the surface of strip steel;
   (d) obtaining a correction function by using a ray emitted by an off-line film thickness detection instrument to excite the two water-soluble chemical substances so as to obtain a characteristic spectrum of the two water-soluble chemical substances where the correction function is obtained by:
      (i) determining the actual film thickness using the first water-soluble chemical substance having an intensive characteristic spectrum relative to the characterstic spectrum of the second water soluble chemical substance;
(ii) determining the measured film thickness using the second water-soluble chemical substance having a weak characteristic spectrum relative to the characteristic spectrum of the first water soluble chemical substance;
(iii) taking the difference between the actual film thickness and the measured film thickness to obtain a thickness correction value; and
(iv) obtaining many thickness correction values corresponding to the many measured film thicknesses to yield a correction function generated by fitting the thickness correction values and measured film thicknesses;
(e) adding the second water-soluble chemical substance having a weak characteristic spectrum into a chromium-free coating liquid, and using a ray emitted by an on-line coating film thickness instrument to excite the substance on the surface of strip steel to obtain the measured film thickness; and
(f) using the correction function and measured film thickness of step (e) to obtain a thickness correction value, whereby the chromium-free coating film thickness on the surface of strip steel is obtained from the measured film thickness and thickness correction value.

2. The on-line detection method of chromium-free coating film thickness on surface of strip steel in claim 1, characterized in that the water-soluble chemical substances which will not react with the chromium-free coating liquid are β-sodium glycerol-phosphate, calcium acetate, titaniumocene complexes, barium chloride or strontium acetate.

3. The on-line detection method of chromium-free coating film thickness on surface of strip steel in claim 1, characterized in that the ray is $\chi$ ray or $\gamma$.

* * * * *